(12) United States Patent
Carlson, Jr. et al.

(10) Patent No.: US 7,253,307 B1
(45) Date of Patent: Aug. 7, 2007

(54) PROCESS FOR PRODUCTION OF METHACRYLIC ACID

(75) Inventors: Curtis Ingstad Carlson, Jr., Houston, TX (US); Michael Stanley DeCourcy, Houston, TX (US); Jamie Jerrick John Juliette, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 266 days.

(21) Appl. No.: 10/987,419

(22) Filed: Nov. 12, 2004

Related U.S. Application Data (63) Continuation of application No. 10/420,580, filed on Apr. 22, 2003, now abandoned.

(60) Provisional application No. 60/376,921, filed on May 1, 2002.

(51) Int. Cl.
*C07C 51/16* (2006.01)
(52) U.S. Cl. .................................... 562/526
(58) Field of Classification Search ............... 562/598, 562/599, 526
See application file for complete search history.

(56) References Cited

U.S. PATENT DOCUMENTS

| | | | |
|---|---|---|---|
| 3,689,541 A | 9/1972 | Sennewald et al. | |
| 3,798,264 A | 3/1974 | Kubota et al. | |
| 3,988,213 A | 10/1976 | Yoshida et al. | |
| 4,199,410 A | 4/1980 | Ohrui et al. | |
| 4,260,821 A | 4/1981 | Benjamin | |
| 5,393,918 A | 2/1995 | Dobson | |
| 2002/0192132 A1 | 12/2002 | Carlson, Jr. et al. | |

FOREIGN PATENT DOCUMENTS

| | | | |
|---|---|---|---|
| EP | 0102642 | | 1/1986 |
| EP | 0656343 | | 6/1995 |
| EP | 0937488 | | 8/1999 |
| EP | 0999200 | * | 5/2000 |
| EP | 1044957 | | 10/2000 |
| EP | 1059281 | | 12/2000 |

* cited by examiner

*Primary Examiner*—Karl Puttlitz
(74) *Attorney, Agent, or Firm*—Marcella M. Bodner (57) ABSTRACT

Provided herein are improved methods for producing methacrylic acid and methacrylate esters using combined or "integrated" processing steps including integrated hydrolysis, integrated cracking systems, and combinations thereof. In one embodiment, other aspects of an methacrylic acid and methacrylate ester production trains are integrated. Also provided are methods to purify crude methacrylic acid streams to form glacial methacrylic acid that is at least 95% pure.

5 Claims, 5 Drawing Sheets

PROCESS FOR PRODUCTION OF METHACRYLIC ACID

CROSS REFERENCE TO RELATED PATENT APPLICATIONS

This non-provisional application is a continuation of non-provisional U.S. patent application Ser. No. 10/420,580, filed Apr. 22, 2003, now abandoned, benefit of which is claimed under 35 U.S.C. § 120 and which in turn claims benefit under 35 U.S.C. § 119(e) of U.S. provisional Application No. 60/376,921, filed May 1, 2002, priority benefit of which is also claimed for the present divisional application.

This invention generally relates to improved high yield production processes for methacrylic acid ("MAA") and methacrylate esters, such as methyl methacrylate ("MMA"). More particularly, according to a preferred embodiment, the present invention relates to an improved process for the high yield production of substantially pure MAA that is at least 95% pure.

Methacrylic acid ("MAA") and methacrylate esters such as methyl methacrylate and butyl methacrylate are used in a wide variety of applications. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. MAA and methacrylate esters are especially prized in these applications and others because of the hardness they impart to the products in which they are used. They also enhance chemical stability and light stability, as well as ultraviolet radiation resistance, when used in certain products. Therefore, MAA and methacrylate esters are often used in applications requiring resins of excellent transparency, strength, and outdoor durability. The MAA and methacrylate ester market is extremely cost-sensitive; thus, any improvement in process yield, however slight, can result in significant cost-savings.

Although other feedstocks, including various $C_4$-based feedstocks, may be used, the most common feedstock for the production of MAA and methacrylate esters has been acetone cyanohydrin ("ACH").

Whereas conventional MAA processes and methacrylate ester processes have very different reaction and purification steps, they do have similar initial processing and valuables recovery operations. For example, the hydrolysis and cracking reactions which are the initial processing steps, are substantially similar. But included in the methacrylate ester reaction and purification operations is an esterification step with an alkanol, a step unnecessary in the reaction and purification of MAA.

Usually, when both MAA and methacrylate esters are produced at the same facility, there is separate production equipment involved (from initial processing through purification) with no cross-over or "integration" between the two processes. In addition to the separate production equipment lines, usually separate operating staffs are employed to run the production lines. Thus, the separate production of each compound results in higher operating costs, capital, and manufacturing costs. Consequently, there is an unaddressed need for a process wherein the suitable steps between the MAA and methacrylate ester production trains are combined or "integrated" so that both products can be produced more economically.

Moreover, the widely used ACH method of producing MAA and methacrylate esters has several disadvantages. For instance, this method produces large amounts of waste sulfuric acid and ammonium bisulfate; the treatment of these byproducts increases production costs. Another disadvantage is that the final crude MAA product stream contains as much as 15% undesirable impurities, such as water, acetic acid, acrylic acid, acetone, methacrylamide (MAM), and α-hydroxyisobutyric acid (HIBA), which are problematic in downstream processes. These undesirable by-products form in the hydrolysis, cracking, and/or reacting steps of the process and may cause the formation of intractable polymer solids in down-stream equipment, resulting in equipment fouling, additional downtime and associated cleanup costs. Heretofore known methods have not been able to remove these impurities from the crude MAA stream efficiently and effectively to produce desirable substantially pure MAA.

Thus, there is an unaddressed need for a method for producing MAA and methacrylate esters using integrated processing steps so that both processes reach maximum economical efficiency. There is also an unaddressed need to produce substantially pure MAA from ACH, which has 5% or less impurities economically and efficiently.

The present invention solves the problems inherent in the prior art by providing methods for producing MAA and methacrylate esters using integrated processing steps, including integrated hydrolysis trains, integrated cracking trains, or a combination thereof. In one of the embodiments of the present invention, additional aspects of the MAA process and the methacrylate ester process are integrated as well.

Another object of the invention is to provide methods and apparatus for producing substantially pure MAA that has 5% or less impurities from a crude methacrylic acid stream.

Thus, provided herein is a process for the preparation of methacrylic acid and esters thereof, the process comprising:
(i) continuously feeding a first raw material comprising acetone cyanohydrin and a second raw material comprising sulfuric acid, oleum or mixtures thereof into a first hydrolysis system;
(ii) continuously feeding a third raw material comprising acetone cyanohydrin and a fourth raw material comprising sulfuric acid, oleum or mixtures thereof into a second hydrolysis system;
(iii) continuously hydrolyzing said first raw material and said second raw material in said first hydrolysis system to form a first hydrolysis product comprising α-sulfatoisobutyramide and α-hydroxyisobutyramide;
(iv) continuously hydrolyzing said third raw material and said fourth raw material in said second hydrolysis system to form a second hydrolysis product comprising α-sulfatoisobutyramide and α-hydroxyisobutyramide;
(v) continuously feeding said first hydrolysis product and said second hydrolysis product to a cracking system;
(vi) continuously cracking said first hydrolysis product and said second hydrolysis product in said cracking system to form a cracking product comprising methacrylamide;
(vii) continuously feeding a first portion of said cracking product and water to an acid formation reactor, while continuously feeding a second portion of said cracking product and an alcohol to an ester formation reactor;
(viii) continuously reacting said first portion of said cracking product and said water in said acid formation reactor to form an acid formation product comprising methacrylic acid;
(ix) continuously reacting said second portion of said cracking product and said alcohol in an ester formation reactor to form an ester formation product comprising an ester of methacrylic acid;

with the proviso that, if said cracking system comprises two or more cracking reactors, in parallel, then a first portion of a cracking product from each of said cracking reactors and water is continuously fed to said acid formation reactor and a second portion of a cracking product from each of said cracking reactors and an alcohol is continuously fed to said ester formation reactor.

Also provided herein is a process for the preparation of methacrylic acid and esters thereof, the process comprising:
(i) continuously feeding a first raw material comprising acetone cyanohydrin and a second raw material comprising oleum into a hydrolysis system;
(ii) continuously hydrolyzing said first raw material and said second raw material in said hydrolysis system to form a hydrolysis product comprising α-sulfatoisobutyramide and α-hydroxyisobutyramide;
(iii) continuously feeding a first portion of said hydrolysis product to a first cracking system, while continuously feeding a second portion of said hydrolysis product to a second cracking system;
(iv) continuously cracking said first portion of said hydrolysis product in said first cracking system to form a first cracking product comprising methacrylamide;
(v) continuously cracking said second portion of said hydrolysis product in said second cracking system to form a second cracking product comprising methacrylamide;
(vi) continuously feeding said first cracking product and water to an acid formation reactor;
(vii) continuously feeding said second cracking product and an alcohol to an ester formation reactor;
(viii) continuously reacting said first cracking product and said water in said acid formation reactor to form an acid formation product comprising methacrylic acid;
(ix) continuously reacting said second cracking product and said alcohol in said ester formation reactor to form an ester formation product comprising an ester of methacrylic acid.

Additionally, provided herein is a process for the preparation of methacrylic acid and esters thereof, the process comprising:
(i) continuously feeding a first raw material comprising acetone cyanohydrin and a second raw material comprising sulfuric acid, oleum or mixtures thereof into a hydrolysis system;
(ii) continuously hydrolyzing said first raw material and said second raw material in said hydrolysis system to form a hydrolysis product comprising α-sulfatoisobutyramide and α-hydroxyisobutyramide;
(iii) continuously feeding said hydrolysis product into a cracking system;
(iv) continuously cracking said hydrolysis product in said cracking system to form a cracking product comprising methacrylamide;
(v) continuously feeding a first portion of said cracking product and water to an acid formation reactor, while continuously feeding a second portion of said cracking product and an alcohol to an ester formation reactor;
(vi) continuously reacting said first portion of said cracking product and said water in said acid formation reactor to form an acid formation product comprising methacrylic acid;
(vii) continuously reacting said second portion of said cracking product and said alcohol in said ester formation reactor to form an ester formation product comprising an ester of methacrylic acid;

with the proviso that, if said cracking system comprises two or more cracking reactors, in parallel, then a first portion of a cracking product from each of said cracking reactors and water is continuously fed to said acid formation reactor and a second portion of a cracking product from each of said cracking reactors and an alcohol is continuously fed to said ester formation reactor.

A more complete understanding of the present embodiments and advantages thereof may be acquired by referring to the following description taken in conjunction with the accompanying drawings, in which like reference numbers indicate like features, and wherein.

Figure 1:
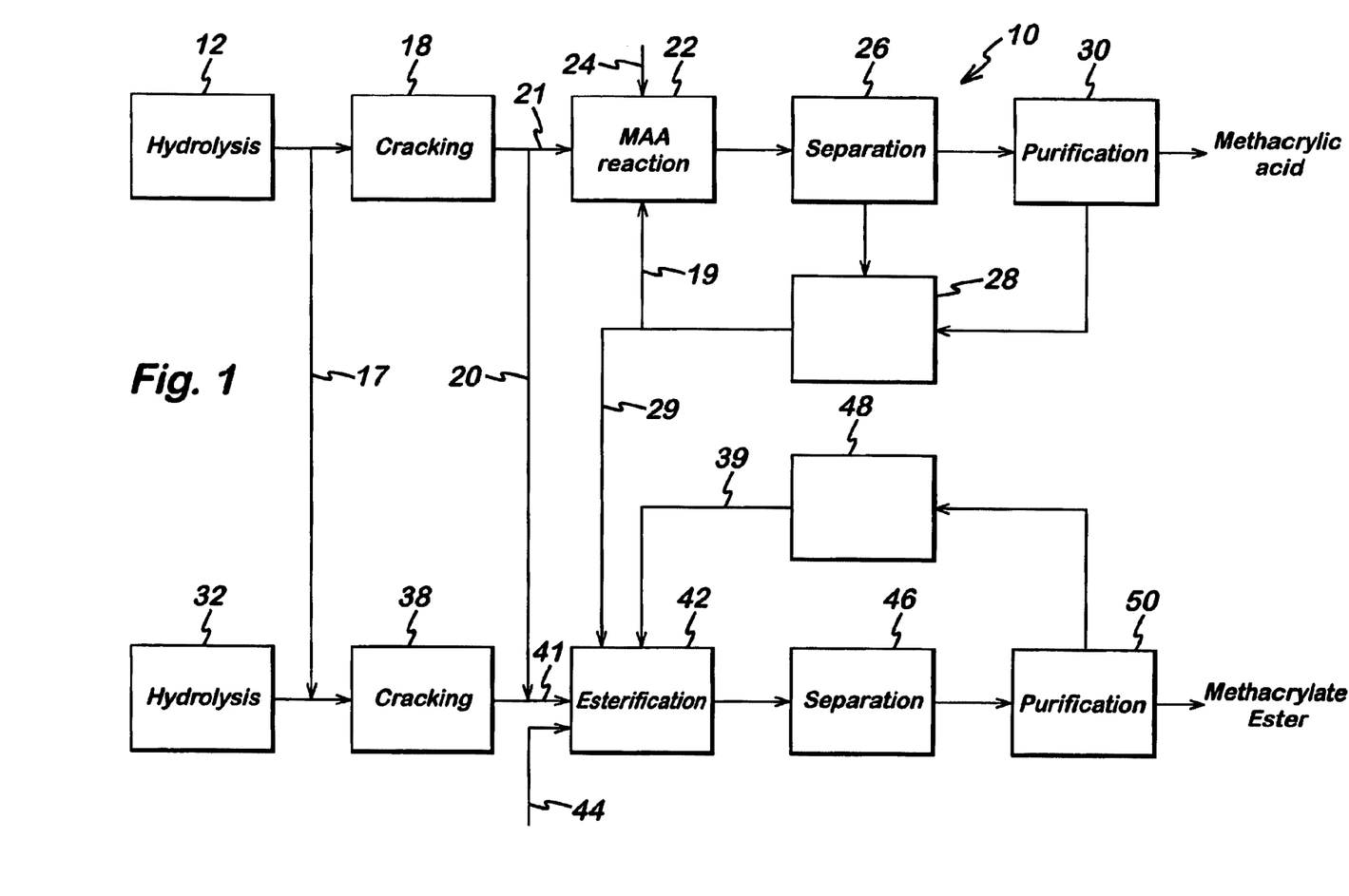
FIG. 1 is a process flow diagram providing an overview of the process of the present invention.

FIG. 1 is a process flow diagram generally providing an overview of the process of the present invention as indicated at 10. There are five basic steps in the process of making MAA and methacrylate esters, namely, hydrolysis, cracking, reaction, separation, and purification. These steps for the MAA process are shown at 12, 18, 22, 26, and 30, respectively, in FIG. 1. These steps for methacrylate esters are shown at 32, 38, 42, 46, and 50, respectively, in FIG. 1. Although only one methacrylate ester train is illustrated in FIG. 1 along side the methacrylic acid train, it is within the scope of the present invention that multiple methacrylate ester trains may be advantageously employed in the methods provided by the present invention. For instance, an ethyl methacrylate train can be employed as well as a methyl methacrylate train with the methacrylic acid train.

The first stage of producing either MAA or methacrylate esters from ACH involves hydrolysis of the ACH in a hydrolysis system; the general chemistry of the hydrolysis process for both MAA and methacrylate esters may be very similar. Shown at 12 and 32 in FIG. 1 is hydrolysis of the ACH in a hydrolysis system to produce a hydrolysis mixture that contains α-sulfatoisobutyramide ("SIBAM") and α-hydroxyisobutyramide ("HIBAM"). ACH and an excess of sulfuric acid are fed into hydrolysis reactor 12. It is preferable to use ACH that has low levels of water and other impurities in the hydrolysis step. The sulfuric acid serves as both a specific reactant and a solvent for the reaction. Using sulfuric acid at concentrations of greater than 95% is also preferred. In an alternative embodiment, oleum or a combination of sulfuric acid and oleum may be used in place of sulfuric acid. Either hydrolysis system may contain a single reactor or multiple reactors connected in series and may also employ one or more reactant addition points.

In the hydrolysis reaction, anhydrous conditions are preferred to minimize the formation of HIBAM, which is more difficult than SIBAM to convert to methacrylamide (MAM).

As opposed to conventional separate production lines for MAA and methacrylate esters, in one embodiment of the present invention the hydrolysis reaction for all of the processes can be combined in hydrolysis reactor 12. When this is done, the hydrolysis step is an "integrated hydrolysis system." Thus, rather than having parallel hydrolysis trains for MAA at 12 and methacrylate esters at 32 that essentially involve at least two lines of the same equipment, in the process of one embodiment of the present invention there need only be one integrated hydrolysis system. This common enterprise can continue through the cracking step and up to the reaction step, as the reaction steps for methacrylate esters and MAA differ. This sharing of equipment results in a substantial cost savings to the manufacturer via reduced capital costs, reduced personnel needs, and reduced long-term operating costs. Also, the manufacturer may achieve additional savings due to the economy of scale achieved by combining the processes.

In one embodiment of the present invention, one to five hydrolysis reactors are connected in series to form an integrated hydrolysis system for both MAA and methacrylate esters production. If multiple reactors are used, it is preferred that a series of two to three reactors is used. Any reactors suitable for conducting hydrolysis reactions that are known in the art, such as a continuous stirred tank reactor, may be used in one embodiment of the present invention as hydrolysis reactor 12. However, such reactors should be resistant to the corrosive effects of the reaction, thus the hydrolysis reactors and reactor ancillaries preferably may be constructed of material resistant to corrosion. The term "reactor ancillaries" means any and all secondary equipment, such as exchangers, instrumentation, mixers and pumps, and associated piping that is connected to the reactor. The term associated piping" includes, but is not limited to, feed lines, bottoms lines, overflow lines, vent lines, inhibitor addition lines, and oxygen addition lines.

Suitable materials of construction resistant to corrosive effects include but are not limited to: stainless steel (e.g., 300 series, 904L, 6-moly), HASTELLOY® (e.g., B, B-2, B-3, C-22, and C-276), tantalum, and zirconium. In some embodiments, the manufacturer may reduce construction costs by utilizing covered base materials. "Covered base materials" are materials that generally are thought not to be corrosion resistant, such as carbon steel, combined with a covering capable of resisting corrosion such as glass, epoxy, elastomer, fluoropolymer (e.g., TEFLON®), or one of the above-listed metals. Covered base materials are constructed by placing a covering capable of resisting corrosion over, and optionally bonding the covering to, the base metal. The covering prevents base-metal contact with the process stream. Covered base-metal construction is especially preferred for large-diameter piping (3.8 cm or larger nominal diameter) and for heat exchanger tubes in high fluid-velocity service (fluid velocity of 0.15 meter/second or more) and other components, where significant metal thickness (3 mm or more metal thickness) may be used to provide structural strength. The materials described above such as stainless steel (e.g., 300 series, 904L, 6-moly), HASTELLOY® (e.g., B, B-2, B-3, C-22, and C-276), tantalum, and zirconium, and covered base-metal materials are hereinafter referred to as "corrosion resistant material."

Hydrolysis is typically conducted at a temperature ranging from 70° C. to 135° C., and preferably from 75° C. to 105° C. Temperatures can be controlled through various means known in the art, such as use of internal cooling coils or recirculation of a portion of the reactor contents through external heat exchangers. The temperature can be held constant throughout the hydrolysis reaction or it can be changed during the course of the reaction, especially when multiple hydrolysis reactors are used in series. If more than one reactor is used, preferably the temperature of the first reactor ranges from 75° C. to 90° C., and the temperature of subsequent reactors ranges from 90° C. to 105° C. The hydrolysis reaction is conducted for a sufficient time to maximize the yield of MAM, SIBAM, and HIBAM. Thus, the reaction time may vary from one minute to an hour.

Further, polymerization inhibitors may be added to the hydrolysis system to prevent polymerization. Suitable locations for adding the inhibitor to the hydrolysis system include but are not limited to the raw material streams upstream of the hydrolysis system, the hydrolysis reactor itself and its reactor ancillaries. If multiple reactors are used and connected in series, then it is preferable to add the inhibitor to the first reactor. However, different inhibitors may be to added to each reactor individually if desired via one inhibitor addition point or multiple inhibitor addition points.

Suitable examples of water-soluble or alcohol-soluble polymerization inhibitors for the hydrolysis system include but are not limited to:
Hydroquinone (HQ);
4-methoxyphenol (MEHQ);
4-ethoxyphenol;
4-propoxyphenol;
4-butoxyphenol;
4-heptoxyphenol;
hydroquinone monobenzylether;
1,2-dihydroxybenzene;
2-methoxyphenol;
2,5-dichlorohydroquinone;
2,5-di-tert-butylhydroquinone;
2-acetylhydroquinone;
hydroquinone monobenzoate;
1,4-dimercaptobenzene;
1,2-dimercaptobenzene;
2,3,5-trimethylhydroquinone;
4-aminophenol;
2-aminophenol;
2-N,N-dimethylaminophenol;
2-mercaptophenol;
4-mercaptophenol;
catechol monobutylether;
4-ethylaminophenol;
2,3-dihydroxyacetophenone;
pyrogallol-1,2-dimethylether;
2-methylthiophenol;
t-butyl catechol;
di-tert-butylnitroxide;
di-tert-amylnitroxide;
2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-amino-2,2,6,6-tetramethyl-piperidinyloxy;
4-ethanoloxy-2,2,6,6-tetramethyl-piperidinyloxy;
2,2,5,5-tetramethyl-pyrrolidinyloxy;
3-amino-2,2,5,5-tetramethyl-pyrrolidinyloxy;
2,2,5,5-tetramethyl-1-oxa-3-azacyclopentyl-3-oxy;
2,2,5,5-tetramethyl-3-pyrrolinyl-1-oxy-3-carboxylic acid;
2,2,3,3,5,5,6,6-octamethyl-1,4-diazacyclohexyl-1,4-dioxy;
salts of 4-nitrosophenolate;
2-nitrosophenol;
4-nitrosophenol;
copper dimethyldithiocarbamate;
copper diethyldithiocarbamate;
copper dibutyldithiocarbamate;

copper salicylate;
methylene blue;
iron;
phenothiazine (PTZ);
3-oxophenothiazine;
5-oxophenothiazine;
phenothiazine dimer;
1,4-benzenediamine;
N-(1,4-dimethylpentyl)-N'-phenyl-1,4-benzenediamine;
N-(1,3-dimethylbutyl)-N'-phenyl-1,4-benzenediamine;
N-nitrosophenylhydroxylamine and salts thereof;
nitric oxide;
nitrobenzene;
p-benzoquinone; or isomers thereof; mixtures of two or more thereof; or mixtures of one or more of the above with molecular oxygen. The polymerization inhibitor is typically used at levels ranging from 100 ppm to 4,000 ppm by weight.

The inhibitor(s) may be added to the hydrolysis reactor alone or may be combined with a suitable solvent and then added to the reactor. Preferred solvents include, but are not limited to, acetone, ACH, trifluoroacetic acid, nitromethane, and/or sulfuric acid. Preferred solvents for use with phenothiazine inhibitors include one or more sulfur compounds. Such sulfur compounds include, but are not limited to, sulfuric acid, sulfur dioxide, methyl sulfone, tetramethylene sulfone ("sulfolane"), and dimethyl sulfoxide ("DMSO").

The product produced by the hydrolysis system is a hydrolysis mixture comprising SIBAM and HIBAM.

Figure 2:
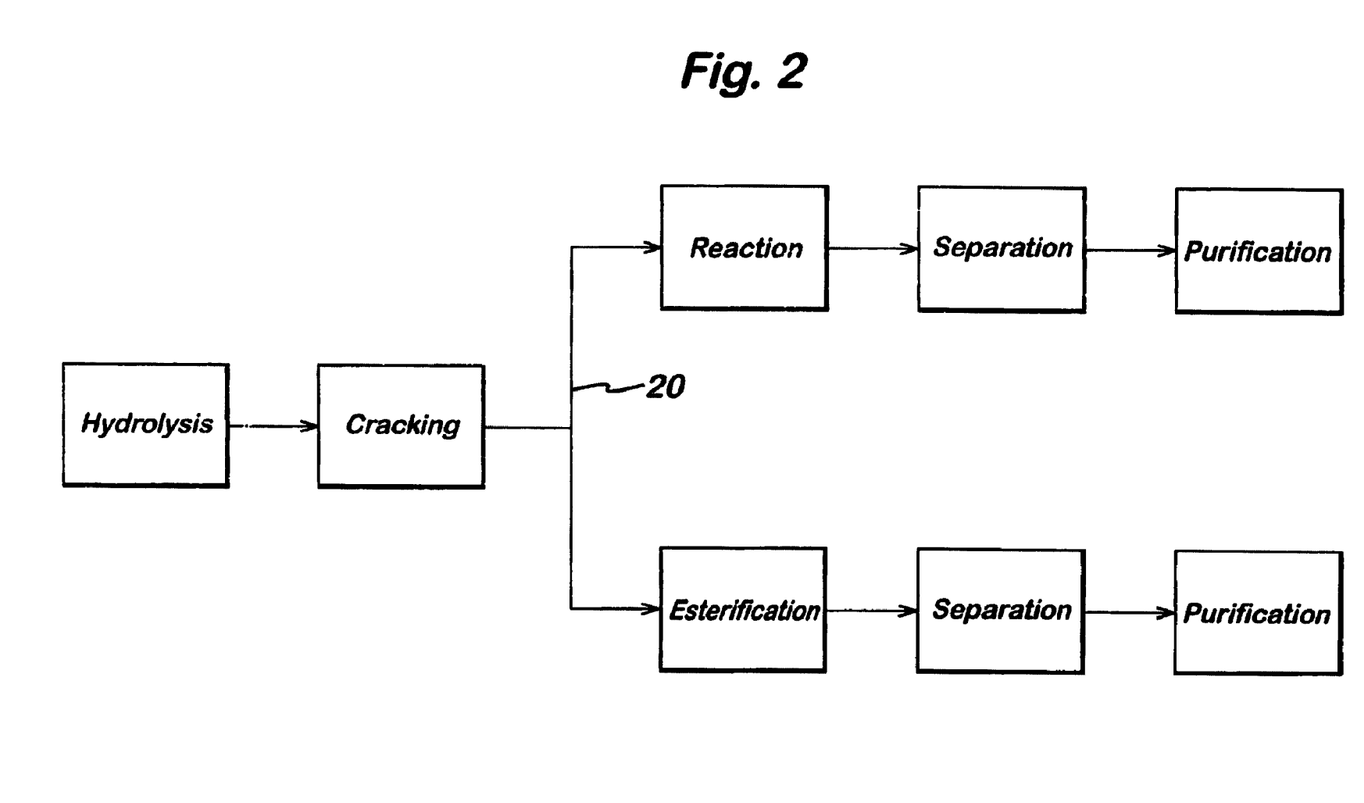
FIG. 2 is a process flow diagram illustrating one embodiment of the present invention wherein both the hydrolysis and cracking systems have been integrated.
Figure 3:
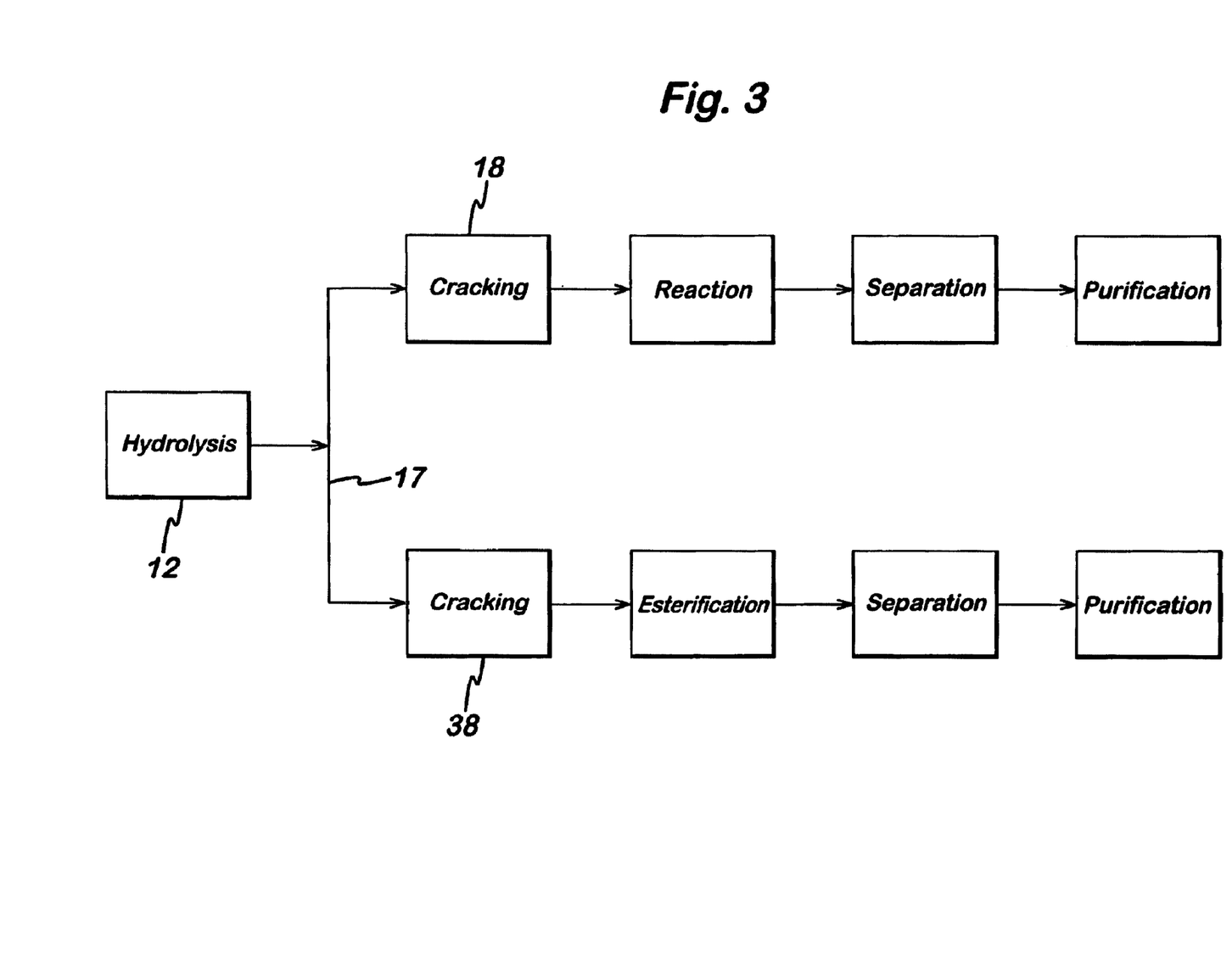
FIG. 3 is a process flow diagram illustrating one embodiment of the present invention wherein the hydrolysis systems are integrated.
Figure 4:
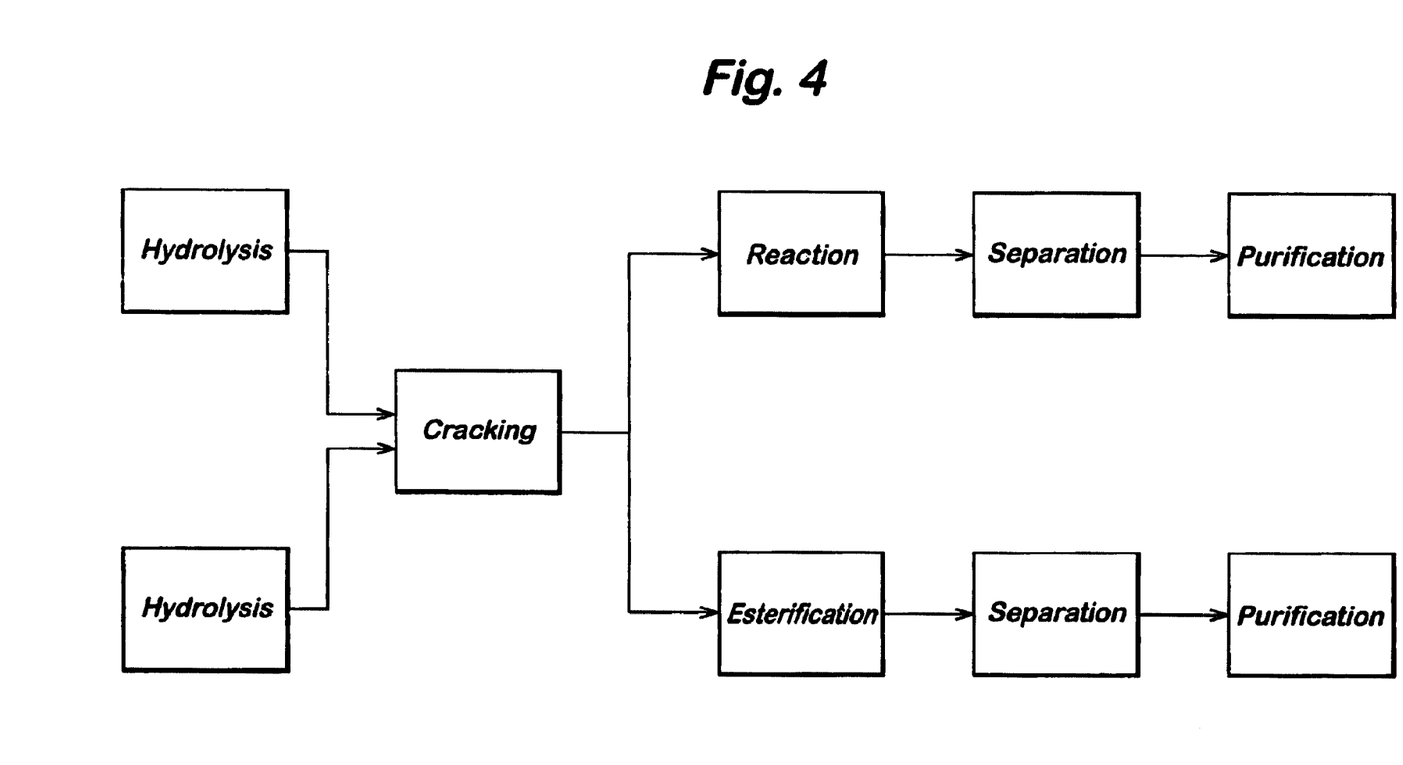
FIG. 4 depicts an alternative embodiment of the process of the present invention wherein the cracking systems are integrated.

The next step in one embodiment of the process of the present invention is cracking the hydrolysis mixture in a cracking train. Provided in one embodiment of the present invention is an integrated cracking train for MAA production and methacrylate esters production. It is contemplated within the present invention that an integrated cracking train may be used even if a common hydrolysis process is not, and vice versa. FIG. 2 illustrates one embodiment of the present invention wherein both hydrolysis and cracking are integrated processes between the MAA production line and the methacrylate ester production line. If hydrolysis is the only integrated process step, then the hydrolysis reactor stream splits at conduit 17. Shown in FIG. 3 is such a process, i.e., where the hydrolysis is the integrated process. If the cracking reaction is also integrated, then the cracker reactor cooler mixture splits at conduit 20 rather than conduit 17. Shown in FIG. 2 is such a process, i.e. where both hydrolysis and cracking are integrated. FIG. 4 depicts another embodiment of the present invention wherein cracking is an integrated process but hydrolysis is not.

If a common integrated cracking train is used for MAA and methacrylate esters, its capacity should be such that it can efficiently process the increased volume of cracker reactor mixture. In an alternate embodiment, multiple smaller cracking trains may be utilized in parallel instead of a single large train to provide the necessary capacity for an integrated cracking system. However, in such an alternate embodiment, the cracking product from each of the cracking reactors is split between the MAA production line and the methacrylate ester production line.

Specifically, incorporated within cracker reactor 18 is a heating unit that may comprise at least one pre-heater and at least one heater or a combination thereof forming a single heating unit. The pre-heater and heater are typically heat exchangers that are utilized to bring the temperature of the hydrolysis mixture up to a sufficient level to facilitate the cracking reaction. The exit temperature of the mixture from the cracker pre-heater is typically from 110° C. to 135° C. The exit temperature of the mixture from the cracker heater ranges from 135° C. to 165° C. Any conventional heat exchanger may be used in the invention provided that it is resistant to high temperature corrosive environments as discussed above. Examples of suitable heat exchangers include plate and frame heat exchangers, plate and fin heat exchangers, spiral heat exchangers, and shell-and-tube heat exchangers. Such heat exchangers are preferably constructed of corrosion resistant materials such as those listed above.

The second part of cracker reactor 18 is a thermal conversion apparatus, preferably, a plug flow reactor. One example of a cracker reactor that is useful in the cracking train of one embodiment of the present invention is disclosed in European Patent Application No. EP 999 200 A1, filed Oct. 22, 1999. Disclosed therein is a suitable plug flow reactor. The third part of cracker reactor 18 is the cracker reactor cooler, which is used to cool the cracker reactor mixture. Cooling the cracker reactor mixture prior to reaction (22 or 42) prevents degradation of the cracked mixture. The cracker reactor cooler may be any type of heat exchanger such as those discussed above, as long as it is resistant to corrosive environments at high temperatures. The exit temperature of the cracker reactor cooler mixture is typically in the range of 90° C. to 110° C.

Conduit 21 carries the cracker reactor cooler mixture to the MAA reactor to continue the MAA process, whereas conduit 41 continues through the methacrylate ester process. In the methacrylate ester process, the next step is contacting the cracker reactor cooler mixture with at least one other stream comprising one or more $C_1$-$C_{30}$ alkanols and optionally water, introduced via conduit 44, to esterification reactor 42, to form the respective methacrylate ester(s). Conduit 44 may comprise one or more addition points for such alkanol streams and they may be located at any desirable location relative to esterification reactor 42. Such alkanols may include but are not limited to: methanol, ethanol, propanol, and butanol. On the other hand, in the MAA reaction step, the strongly acidic cracker reactor cooler mixture (which contains MAM among other things) is reacted in MAA reactor 22 with a water component that is introduced into MAA reactor 22 via conduit 24. MAA reactor 22 is operated at a pressure of 3.7 atm to 7.8 atm; more preferably at 4.4 atm to 7.1 atm; and, most preferably at 5.1 atm to 6.4 atm. The reaction is performed at a temperature at 50° C. to 210° C., more preferably at 70° C. to 190° C., most preferably at 80° C. to 170° C.

In the MAA reaction process, it is preferred that the stoichiometric reactor feed ratio of water to MAA reactor 22 be measured against the ACH feed to hydrolysis reactor 12. Preferably, this ratio may be 9 moles of water/mole of ACH to 4 moles of water/mole of ACH; more preferably 8 moles of water/mole of ACH to 5 moles of water/mole of ACH; most preferably at 7 moles of water/mole of ACH to 6 moles of water/mole of ACH. We have found, however, that below a ratio of 4, the corrosion rate of the reactor mixture is high, and consequently, significant damage to MAA reactor 22 and its reactor ancillaries may result. The water that is added may be fresh, recycled, or a combination of fresh and recycled water. The term "recycled water" includes a stream comprising water and compatible recovered organics, such as MAA. A suitable source of recycled water is valuables recovery 28. If recycled water is used, the manufacturer realizes an overall yield improvement. Also, if recycled water is used, it is preferable to store it in a tank that is operably connected to MAA reactor 22. This recycled water tank may contain a spray ring apparatus in the vapor space of the tank to facilitate the removal of condensed polymerizable monomers from the interior surfaces of the vapor space to prevent agglomeration on those surfaces. If such an apparatus is used, it is preferable that a fluid spray, that may comprise a gas or a liquid, from the apparatus be directed toward the roof and the inside surfaces of the tank. The spray apparatus may be operated continuously or intermittently, as required. Any gas or liquid comprising materials compatible with the operation of the MAA reactor may be employed for the fluid spray; examples of suitable materials include but are not limited to air, vapor phase inhibitors, water, MAA and acetone. In some embodiments, the fluid spray may comprise recycled water. The fluid spray may optionally be passed through a heat exchanger to control its temperature and may optionally comprise one or more polymerization inhibitors, such as those previously described. Furthermore, such a spray system may also be advantageously employed in other vessels involved in the processes of the present invention used to produce MAA or methacrylate esters including any or all of the: hydrolysis reactors, continuous stirred tank reactors, horizontal separators, condensers, distillation columns, and/or product storage tanks. Further, this concept is envisioned to be applicable to the production and storage of other monomers, which may be subject to or plagued by the problems associated with condensation polymerization. Examples of such processes include but are not limited to production of other vinyl monomers.

In an alternate embodiment, recycled water (from, for example, a recycled water tank that is supplied by valuables recovery 28) may be supplied to a methacrylate ester process at esterification reactor 42 rather than the MAA process reactor. In a preferred embodiment, the recycled water tank is an integrated water tank, feeding recycled water for both the production of MAA and methacrylate esters. Similarly, a recycled water tank such as that described above may be employed in methacrylate ester production. A suitable source of recycled water is valuables recovery 48. If such a tank is used, it may also be advantageous to add alkanols directly to this tank either in addition to or instead of utilizing stream 44. If the recycled water tank is an integrated water tank, recycled water is supplied to both the esterification reactor in the methacrylate ester process as well as the MAA reactor in the MAA process. However, due to the chemical differences between MAA and its esters, an integrated recycled water tank is most useful when the recycled water is generated by both the MAA production process (such as in valuables recovery 28) and the ester production process (such as at 48) but only consumed in the methacrylate ester process. Organics in the recycled water produced in the methacrylate ester process may not be suitable for use in the MAA reactor.

In some embodiments, recycled water tanks such as those described above may be used to recover recycled water streams from sources in other production processes, such as for example, ACH, (meth)acrylonitrile (e.g. cyanide-bearing water streams), or transesterification processes (e.g. methanol-bearing distillates). It is envisioned that many other compatible water streams may similarly be suitable in the methods of the present invention.

The addition of polymerization inhibitors upstream of or directly to MAA reactor 22 or methacrylate ester process esterification reactor 42 may be useful to prevent polymerization. The inhibitor may be a water soluble or alcohol soluble polymerization inhibitor. Suitable examples include those listed above. Mixtures of two or more of these inhibitors, or mixtures of one or more of these inhibitors combined with molecular oxygen may be used. The polymerization inhibitor is typically used at levels ranging from 100 ppm to 4,000 ppm by weight. The inhibitor may be added with or without a suitable diluent.

Conventional continuous stirred tank reactors are suitable in one embodiment of the present invention for MAA reactor 22 and esterification reactor 42. As to MAA reactor 22 we have found, however, that the MAA reaction mixture is actually a single-phase system that does not require mixing; therefore, the use of a simpler, less-expensive plug flow reactor is preferred as MAA reactor 22. In one embodiment, such a plug flow reactor may comprise a cylindrical vessel with optional internals such as distributors or baffles. One embodiment of the present invention uses a plug flow reactor that comprises one or more straight piping runs. If such a plug flow reactor is used, the length of the pipe may be sufficient to maximize the yield of MAM to MAA. Thus, the residence time may vary from one minute to thirty minutes or more. Plug flow in MAA reactor 22 may generally be maintained by use of design features such as those described with respect to the cracking section. For optimum reactor design, a pipe having minimal turns is preferred. If turns are required for plant spacing or other reasons, such turns should be designed to achieve close to plug flow. The diameter of the pipe may be selected so as to favor plug flow as well. The pipe may also be straight, e.g. no turns, in which case, plug flow is maintained. An alternative to having smooth turns in the pipe while maintaining plug flow is to have a CRV™ in each turn. Heat-treated zirconium is a corrosion resistant material particularly suited to be the construction material for MAA reactor 22 and esterification reactor 42.

After the reaction step, the MAA reactor mixture (which comprises MAA) passes to separation step 26 and is cooled in at least one heat exchanger to 50° C. to 95° C. At this temperature range, the single-phase MAA reactor mixture will separate into a MAA product stream and a lower layer sulfur-bearing residue stream. The separation is essentially a buoyancy separation. Suitable separation vessels include, but are not limited to, settling tanks, cyclones, and gravity separators. The separation vessel may include internal components. Internal components include but are not limited to packing, baffles, stilling plates, spray rings, spray nozzles, or weirs. Any type of conventional heat exchanger may be used in the separation step, provided that it is resistant to high-temperature corrosive environments as discussed above. Examples of suitable heat exchangers include plate and frame heat exchangers, plate and fin heat exchangers, spiral heat exchangers, and shell-and-tube heat exchangers. Such heat exchangers are preferably constructed of corrosion resistant materials. Heat treated zirconium is a corrosion resistant material particularly suited to these heat exchanger (s). The temperature of the separation vessel optionally may be increased at short intervals during the separation to reduce the impact of polymer formation in the heat exchanger/separator.

The lower layer sulfur-bearing residue stream from separation 26 may be treated in valuables recovery 28. Valuables recovery 28 can have several embodiments; examples of valuables recovery embodiments suitable for use in the present invention are disclosed in U.S. Patent Publication No. US 2002/0192132, published on Dec. 19, 2002. Organics and water that are recovered in valuables recovery 28 can be recycled (for example, back to MAA reactor 22) to increase overall yield. After treatment, the remainder of the sulfur-bearing residue stream minus recovered organics and water can be sent to further processing operations, including sulfuric acid production and ammonium sulfate production, or to disposal.

Unlike the sulfur-bearing residue treatment process in methacrylate esters production, however, we have found that it may be useful to add an antifoaming agent to the lower layer sulfur bearing residue stream treatment vessel in the MAA process following the separation step. One example of a suitable antifoaming agent is Map EC9055A, available from Nalco-Exxon, but other commercially available agents may be utilized. As a general guideline, a sufficient quantity of antifoaming agent is 4.2 liters per 100,000 kg of sulfur-bearing residue stream fed to the valuables recovery process. The quantity of antifoaming agent may be reduced or eliminated, however, depending on the composition of the stream being treated. Typically, the crude MAA product stream from separation 26 contains 80% or more MAA, as well as MAM, hydroxy isobutyric acid ("HIBA"), water, and other trace components. If desired, the crude MAA can be used as a final product even though it contains greater than 5% impurities; however, it is advantageous to further process crude MAA to a 95% or higher purity product stream. Further, it is noteworthy that, while crude MAA streams derived from non-ACH processes may have significantly different concentrations of MAA in them, such streams may also benefit from the purification aspect of the present invention to produce a 95% or higher purity product stream.

Before further purification, the crude MAA stream from separation 26 may optionally be stored in an MAA storage system. If stored, it is preferable to cool the crude MAA stream prior to storage to inhibit polymerization and reduce the corrosive effects of the crude MAA on the storage equipment. Cone bottom crude tanks for storage are preferred and may be constructed of or lined with corrosion-resistant materials such as stainless steel (e.g., 300 series, 904L, 6-moly), Hastelloys (e.g., B, B-2, B-3, C-22, and C-276), tantalum, graphite, vinyl ester resin, Teflon, fiberglass, glass, or epoxy. Storing the crude MAA provides settling time in which an additional sulfur-bearing residue lower layer may form. If it forms, this additional lower layer may be easily removed via the conical bottom outlet of the tank, and transferred back to valuables recovery 28 as discussed above with respect to the original lower layer sulfur-bearing residue stream. Removing the additional lower layer in this manner protects downstream purification equipment from the corrosive effects of this sulfur-bearing residue stream. Additionally, such storage tanks give the manufacturer the ability to run the front end of the process independent of the back purification end. Crude MAA streams comprising MAA and impurities may be further processed in purification system 30 if desired to obtain substantially pure MAA that is at least 95% pure; such substantially pure MAA streams are herein referred to as Glacial Methacrylic Acid ("GMAA"). One embodiment of purification system 30 is shown schematically in FIG. 5. Note that the crude MAA feed stream 300 may also originate from a non-ACH based process, e.g. an isobutane/isobutylene-based process, an ethylene-based process, or an ACH based process not containing integrated processing steps.

Figure 5:
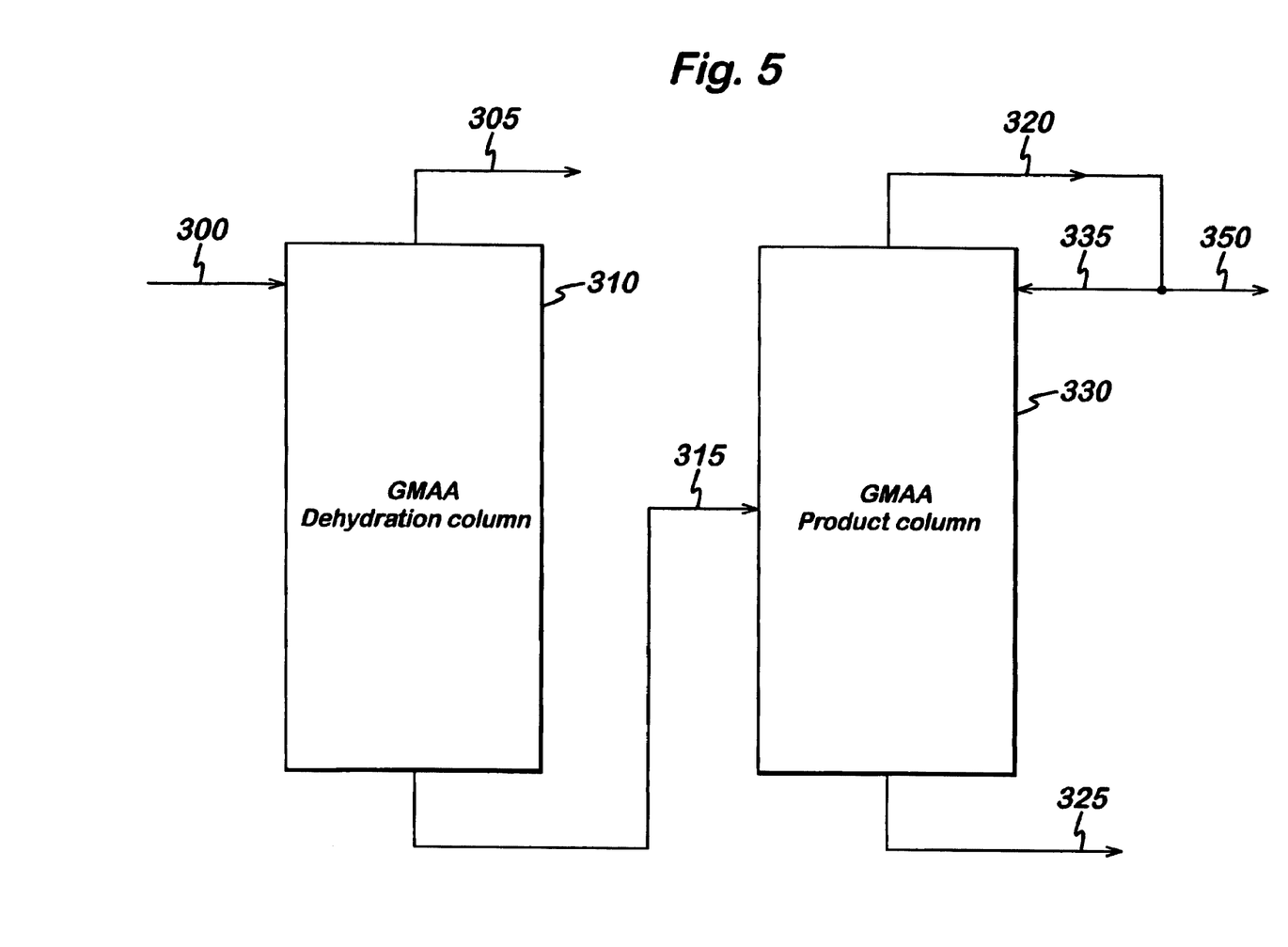
FIG. 5 is an illustration of one embodiment of the method of the present invention to produce methacrylic acid having a purity of at least 95%.

To produce GMAA, in one embodiment of the purification aspect of the present invention shown in FIG. 5, a series of columns may be used. The first column used in the purification system is a GMAA dehydration column. A crude MAA product stream is provided via line 300 to GMAA dehydration column 310, wherein light ends such as acetone and water are removed overhead via line 305. The GMAA dehydration column and its column ancillaries are preferably constructed of corrosion resistant materials. The GMAA dehydration column ancillaries include any and all secondary equipment, such as vacuum equipment, reboilers, condensers and pumps, and associated piping. By associated piping is meant piping that is connected to the column or any secondary equipment, including but not limited to feed lines, bottoms lines, overheads lines overflow lines, vent lines, inhibitor addition lines, oxygen addition lines, reflux lines, and rundown lines.

Suitable materials of construction for the GMAA dehydration column and its column ancillaries include, but are not limited to: stainless steels (e.g., 300 series, 904L, 6-moly), HASTELLOY® (e.g., B, B2, B3, C-22 and C-276), tantalum and zirconium.

In some embodiments, the manufacturer may reduce construction costs by utilizing base metals, such as carbon steel, combined with a corrosion-resistant covering—such as glass, epoxy, elastomer, fluoropolymer (e.g., TEFLON®), or one of the above listed metals—as a material of construction. In such instances, the covering is placed over, and may be optionally bonded to, the base metal to prevent base metal contact with the process stream; this is herein referred to as covered base metal construction. Covered base metal construction is preferred for large diameter piping (3.8 cm or larger nominal diameter) and for heat exchanger tubes in high fluid velocity service (fluid velocity of 0.15 meter/second or more). Covered base metal construction is especially preferred for pressure-containing vessels, as well as manway covers, flange covers, heat exchanger tubesheets, and other components, where significant metal thickness (3 mm or more metal thickness) is used to provide structural strength.

Internal components such as trays or packing may be useful in GMAA dehydration column 310. If used, trays are preferred; if trays are used, it is preferable to use two to ten perforated plate trays. Internals, if present, may be made from the same materials as the column itself or may be constructed from one or more different materials; for example, 300 series stainless steel may be used for the trays and the column may be made of HASTELLOY®.

Preferably, the GMAA dehydration column is operated in such a way that the bottoms temperature is minimized, for example, such as under a vacuum. In a preferred embodiment, the pressure at the bottom of the column is maintained at 50 mmHg to 80 mmHg, which allows the bottom of the column to be operated at a temperature of 70° C. to 110° C. At least one heat exchanger may be used as the heating apparatus for the GMAA dehydration column. Desuperheated steam is the preferred source of heat for such heat exchangers. If a reboiler is used as the heat exchanger, it may be internal or external to the distillation column. Vortex breakers are also useful in the bottom of the GMAA dehydration column.

It is oftentimes useful to add one or more inhibitors such as those listed above to the GMAA dehydration column with or without a diluent. Hydroquinone ("HQ") inhibitor is a preferred inhibitor and may be added directly, or with a diluent such as water, in one or more locations throughout the distillation column and its ancillaries. If used, it is preferred that the HQ inhibitor be added at a rate of 1 kg to 10 kg of HQ per 10,000 kg of GMAA dehydration column feed; more preferably from 1.3 kg to 8 kg of HQ per 10,000 kg of GMAA dehydration column feed; and most preferably from 1.5 kg to 5 kg of HQ per 10,000 kg of GMAA dehydration column feed. If HQ is used, it is further preferred that an oxygen-containing gas be added in one or more locations throughout the GMAA dehydration column and its ancillaries to enhance the effectiveness of the HQ inhibitor. The term "oxygen-containing gas," as used herein, refers to any gas comprising oxygen.

The light ends are taken off of the top of the GMAA dehydration column 310 via line 305 and recycled for use elsewhere in an MAA process or a methacrylate ester process (in an integrated facility producing both MAA and methacrylate esters). The stream may also be routed to an acetone recovery vessel. A partial-condenser arrangement is preferred, however, wherein stream 305 is divided into two or more streams, including at least one MAA/water stream and one water/acetone stream. In this way, the MAA/water stream can be recycled directly into the MAA process and/or the methacrylate ester process and the water/acetone stream can be routed to another process such as an acetone recovery operation, a scrubber, or a flare. If the MAA/water stream is condensed after removal from the GMAA dehydration column, tempered water having a temperature above 16° C. may be used in the condenser to avoid freezing MAA in the stream. The preferable range for the tempered water is 16° C. to 35° C. In a preferred embodiment, a portion of the condensate is recirculated back to the condenser and optionally to the vapor inlet line, to minimize fouling and improve condenser efficiency. The condensate may flow freely out of the recirculation line or may be sprayed onto the tubesheet, condenser interior surfaces, and/or inlet vapor line interior walls. If inhibitor is added to the condenser, it may be added to this condensate recirculation stream to improve the distribution of the inhibitor. In an especially preferred embodiment, at least a portion of this condensate recirculation stream may pass through a spray ring of the type previously described to wash polymerizable condensates from the interior surfaces of the GMAA dehydration column, its condensers, and/or interconnecting vapor lines. To minimize condensation polymerization, vapor spaces on the GMAA dehydration column, its condensers, and interconnecting vapor lines are preferably maintained at a temperature above the dew point of MAA; insulation and electric or steam tracing are effective for this purpose.

The glacial methacrylic acid dehydration column product stream 315 contains some HIBA, but has lost a substantial amount of acetone and water. It is fed to a second distillation column referred to herein as GMAA product column 330. In GMAA product column 330, MAA is further separated from various impurities to produce GMAA. The GMAA product column 330 and its column ancillaries are preferably constructed of corrosion resistant materials. The GMAA dehydration column ancillaries include any and all secondary equipment, such as vacuum equipment, reboilers, condensers and pumps, and associated piping. By associated piping is meant piping that is connected to the column or any secondary equipment, including, but not limited to feed lines, bottoms lines, overheads lines overflow lines, vent lines, inhibitor addition lines, oxygen addition lines, reflux lines, and rundown lines.

Suitable materials of construction for the GMAA dehydration column and its column ancillaries include, but are not limited to: stainless steels (300 series, 904L, 6-moly), HASTELLOY® (e.g., B, B2, B3, C-22 an C-276), tantalum and zirconium.

In some embodiments, the manufacturer may reduce construction costs by utilizing base metals, such as carbon steel, combined with a corrosion-resistant covering—such as glass, epoxy, elastomer, fluoropolymer (e.g., TEFLON®), or one of the above listed metals—as a material of construction. In such instances, the covering is placed over, and may be optionally bonded to, the base metal to prevent base metal contact with the process stream; this is herein referred to as covered base metal construction. Covered base metal construction is preferred for large diameter piping (3.8 cm or larger nominal diameter) and for heat exchanger tubes in high fluid velocity service (fluid velocity of 0.15 meter/second or more). Covered base metal construction is especially preferred for pressure-containing vessels, as well as manway covers, flange covers, heat exchanger tubesheets, and other components, where significant metal thickness (3 mm or more metal thickness) is used to provide structural strength. Internal components such as trays or packing may be used in GMAA product column 330, if desired. Trays are preferred; if trays are used, it is preferable that five to fifteen perforated plate trays are used. Internals, if present, may be made from the same materials as the column itself or may be constructed from one or more different materials. For example, 300 series stainless steel may be used for both the internals and the column.

GMAA product column 330 may be operated such that the decomposition of HIBA is avoided. Preferably, the product column can be operated under a vacuum (i.e., below atmospheric pressure) to minimize the temperature at the bottom of the column. For example, in one embodiment, the pressure at the bottom of the column is maintained below 150 mmHg, allowing the bottom of the column to be operated below 125° C. In a preferred embodiment, the pressure at the bottom of the column is maintained below 70 mmHg, and the bottom of the column is operated below 110° C. At least one heat exchanger may be used as the heating apparatus for the GMAA product column. Desuperheated steam is preferred as the heat exchanger's heat source. If a reboiler is used as the heat exchanger, it may be internal or external to the column. Vortex breakers are also useful in the bottom of the GMAA product column.

Although it may be within the scope of one embodiment of the present invention to combine the GMAA dehydration column and the GMAA product column or to subdivide either one of them into one or more sequential columns, two distillation columns are generally most useful in the process. If a single column is used it is referred to as a glacial methacrylic acid dehydration-product column.

GMAA having a purity level greater than or equal to 95% leaves product column 330 via line 320. It is at least partially condensed. Tempered water, as discussed above, may be used in the condenser to avoid freezing the MAA in the stream. In order to maintain the required purity of the GMAA product, it is often necessary to return a portion of the condensate back to the product column via reflux line 335; the fraction of condensate returned may vary from 0% to 100%, depending on the operating conditions of the product column and the GMAA purity level desired. The remaining condensate is then transferred via line 350 to GMAA product storage. In a preferred embodiment, a portion of the condensate is recirculated back to the condenser, and optionally to the vapor inlet line, to minimize fouling and improve condenser efficiency. The condensate may flow freely out of the recirculation line or may be sprayed onto the tubesheet, condenser interior surfaces, and/or the inlet vapor line. If inhibitor is added to the condenser, it may be added to the condensate recirculation stream to improve the distribution of the inhibitor. In an especially preferred embodiment, at least a portion of this reflux condensate recirculation stream may pass through a spray ring of the type previously described to wash polymerizable condensates from the interior surfaces of the product column, its condensers, and/or interconnection vapor lines.

MAA, HIBA, and other impurities (oftentimes referred to as heavy ends) are removed from the bottom of the product column via line 325 and may be combined with other sulfur-bearing residue streams in values recovery 28 (FIG. 1), or may be routed to a recycle stream in the methacrylate esters process (in an integrated facility producing both MAA and methacrylate esters). The bottoms line 325 is preferably constructed of corrosion resistant materials. The GMAA product column bottoms stream may also be disposed of, but preferably fuel values may be recovered before disposal. Optionally, the GMAA product column bottoms can be further processed in an independent stripping system to recover residual MAA, prior to combining it with the sulfur-bearing residue streams. In one embodiment of an independent stripping system, the GMAA product column bottoms are heated in one or more glass-lined stripping vessels with live steam. Live steam is steam that comes into direct contact with the MAA-containing product column bottoms stream. It is preferred that the stripping vessels be operated at subatmospheric pressure to maximize the recovery of MAA. The recovered MAA may be recycled back into the MAA process, for example, via the recycle water tank. The residue from the stripping vessel, substantially free of residual MAA, may then be combined with the sulfur-bearing residue streams for values recovery 28 (FIG. 1) or may be routed to the methacrylate esters process in an integrated facility producing both MAA and methacrylate esters.

To minimize condensation polymerization, vapor spaces on the GMAA product column, its condensers, and interconnecting vapor lines are preferably maintained at a temperature above the dew point of MAA; insulation and electric or steam tracing are suitable for this purpose.

It is oftentimes useful to add inhibitors such as those listed above to the GMAA product column optionally with a diluent. Methyl ether of hydroquinone ("MEHQ") inhibitor is especially preferred and may be added directly, or with a diluent such as MAA, in one or more locations throughout the GMAA product column and its ancillaries. If used, it is preferred that the inhibitor be added at a rate of 1 kg to 15 kg of MEHQ per 10,000 kg of GMAA dehydration column feed; more preferably at a rate of 1.5 kg to 12 kg of MEHQ per 10,000 kg of GMAA dehydration column feed; most preferably at a rate of 2 kg to 9 kg of MEHQ per 10,000 kg of GMAA dehydration column feed. Optionally, a variable amount of additional inhibitor may be added directly to the product rundown line to ensure that the product-stream inhibitor concentration is within final product specifications. The specific amount of inhibitor to be added may be determined by analyzing samples of the product stream for inhibitor concentration manually and/or with in-line process analyzers, and adjusting the addition rate accordingly. If more than one inhibitor is introduced directly into the product column, the addition rates of the individual inhibitors may be reduced relative to the rates disclosed above. If MEHQ inhibitor is used, it is further preferred that oxygen-containing gas be added to the distillation column to enhance the effectiveness of the MEHQ inhibitor. Oxygen-containing gas may be added in one or more locations throughout the distillation column and its ancillaries.

The addition of oxygen-containing gas is especially advantageous for phenolic inhibitors, such as HQ and MEHQ. Operating temperatures and pressures impact the flammability limits and oxygen solubility within the purification system, and these properties should be taken into account when determining the appropriate oxygen concentration to be used for the oxygen-containing gas. Considerations of such factors are within the ability of one of ordinary skill in the art, and either pure oxygen or atmospheric air may be commonly employed.

Surprisingly, we have found that there may be an important factor affecting the efficacy of inhibition within the purification systems not previously considered with respect to oxygen addition—that is the avoidance of high oxygen concentrations within the monomer-containing solution itself. When oxygen concentrations are large relative to inhibitor concentrations, oxygen can actually increase the rate of polymerization by promoting the formation of peroxide and, ultimately, monomer radicals. For this reason, it is not recommended that oxygen-containing gas be added when no inhibitor is present. We have determined that the optimal oxygen to inhibitor ratio will vary with respect to the inhibitor used, as well as the residence time within the purification system. Specifically, when HQ is the selected inhibitor, it is preferred that the ratio of the oxygen-containing gas feed to the HQ inhibitor feed added to the purification system is maintained at 0.65 mole to 10 moles of $O_2$/mole of HQ; more preferably at 1 mole to 8.5 moles of $O_2$/mole of HQ; most preferably at 1.5 moles to 6 moles of $O_2$/mole of HQ. When MEHQ is the selected inhibitor, it is preferred that the ratio of oxygen-containing gas feed to the MEHQ inhibitor feed added to the purification system be maintained at 1 mole to 11.5 moles of $O_2$/mole of MEHQ; more preferably at 1.5 moles to 9 moles of $O_2$/mole of MEHQ; most preferably at 2 moles to 6 moles of $O_2$/mole of MEHQ.

By way of example and not limitation, the following description, relating to the operation of the GMAA purification system that is within the scope of this invention, is provided to illustrate the use of the inhibitor in conjunction with an oxygen-containing gas:

EXAMPLE 1

A crude MAA feed stream, comprising greater than 80% MAA, is fed to a GMAA dehydration column at a rate of 4,545 kg/hr. The pressure at the bottom of the column is 65 mmHg and the temperature at the bottom of the column is maintained at 90° C. to 100° C. Inhibitor solution comprising 3.5% HQ in water is added in multiple locations throughout the GMAA dehydration column and its ancillaries to yield an overall solution feed rate of 23 kg/hr. Atmospheric air is added to the reboiler circulation line at a rate of 5 kg/hr. The resultant ratio of oxygen-containing gas addition to inhibitor is 4.5 moles $O_2$ per mole of HQ, and polymer formation in the distillation column is effectively inhibited.

EXAMPLE 2

An MAA feed stream, comprising greater than 90% MAA, is fed to a GMAA product column at a rate of 9,090 kg/hr. The pressure at the bottom of the column is 60 mmHg and the temperature at the bottom of the column is maintained at 100° C. to 105° C. Inhibitor solution comprising 2.5% MEHQ in GMAA is added in multiple locations throughout the GMAA product column and its ancillaries to yield an overall solution feed rate of 126 kg/hr. Atmospheric air is added to the reboiler circulation line at a rate of 9 kg/hr. The resultant ratio of oxygen-containing gas addition to inhibitor is 2.6 moles $O_2$ per mole of MeHQ, and polymer formation in the distillation column is effectively inhibited.

The present invention, therefore, is well adapted to carry out the objects and attain both the ends and the advantages mentioned, as well as other benefits inherent therein. While the present invention has been depicted, described, and is defined by reference to particular embodiments of the invention, such references do not imply a limitation on the invention, an no such limitation may be inferred. The invention is capable of considerable modification, alteration, and substitution of equivalents in form and/or function, as will occur to those of ordinary skill in the pertinent arts. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A process for the preparation of methacrylic acid comprising:
   (i) providing a first raw material comprising acetone cyanohydrin and a second raw material comprising a material selected from the group consisting of oleum and a combination of sulfuric acid and oleum;
   (ii) hydrolyzing said first raw material and said second raw material to form a hydrolysis product;
   (iii) cracking said hydrolysis product to form a cracking product;
   (iv) reacting said cracking product and water in a plug flow acid formation reactor to form an acid formation product comprising methacrylic acid, wherein said acid formation reactor is maintained at a pressure of from 3.7 atmospheres to 7.8 atmospheres and a temperature between 80° C. and 170° C.; and
   (v) cooling said acid formation product to a temperature between 50° C. and 95° C. to form a two-phase product stream which is separable by gravitational settling.

2. The process as claimed in claim 1, wherein step (iv) further comprises maintaining said acid formation reactor at a temperature of from 95° C. to 170° C. to maintain said cracking product and water in a single phase stream.

3. The process as claimed in claim 1, wherein said water is provided to said plug flow acid formation reactor at a ratio of from 4 to 9 moles of water per mole of said first raw material provided in step (i).

4. A process for the preparation of methacrylic acid comprising:
   (i) providing a first raw material comprising acetone cyanohydrin and a second raw material comprising a material selected from the group consisting of oleum and a combination of sulfuric acid and oleum;
   (ii) hydrolyzing said first raw material and said second raw material to form a hydrolysis product;
   (iii) cracking said hydrolysis product to form a cracking product; and
   (iv) reacting said cracking product and water in a plug flow acid formation reactor to form an acid formation product comprising methacrylic acid, wherein acid formation reactor is maintained at a pressure of from 3.7 atmospheres to 7.8 atmospheres and a temperature between 80° C. and 170° C., and wherein said water is provided to said plug flow acid formation reactor at a ratio of from 4 to 9 moles of water per mole of said first raw material provided in step (i).

5. The process as claimed in claim 4, further comprising the step of cooling said acid formation product to a temperature between 50° C. and 95° C. to form a two-phase product stream which is separable by gravitational settling.

* * * * *